United States Patent [19]

Guenin et al.

[11] Patent Number: 6,036,964
[45] Date of Patent: Mar. 14, 2000

[54] PERSONAL HYGIENE PRODUCT WITH ENHANCED FRAGRANCE DELIVERY

[75] Inventors: Eric P. Guenin, Hopewell Township; John C. Brahms, Piscataway; Anne Elisabeth Vickery Gale, Landing; Patricia Ann Hall-Puzio, Succasunna; Peter R. Hilliard, Far Hills; Gail Sharon Klewsaat, Neshanic Station; Cuthbert Donald Taylor, Kendall Park; Paul Joseph Vincenti, Jefferson, all of N.J.

[73] Assignee: Colgate-Palmolive Company, New York, N.Y.

[21] Appl. No.: 09/035,252

[22] Filed: Mar. 5, 1998

[51] Int. Cl.⁷ ....................................................... A61K 6/00
[52] U.S. Cl. ........................... 424/401; 424/76.1; 424/65; 424/420
[58] Field of Search ................................... 424/401, 76.1, 424/65, 420

[56] References Cited

U.S. PATENT DOCUMENTS

| | | |
|---|---|---|
| 4,268,498 | 5/1981 | Gedeon et al. . |
| 5,200,174 | 4/1993 | Gardlik et al. . |
| 5,270,034 | 12/1993 | Cheng . |
| 5,284,649 | 2/1994 | Juneja . |
| 5,409,694 | 4/1995 | Meyer et al. . |
| 5,417,964 | 5/1995 | Carlson, Sr. et al. . |
| 5,424,070 | 6/1995 | Kasat et al. . |
| 5,487,887 | 1/1996 | Benfatto . |
| 5,490,979 | 2/1996 | Kasat et al. . |
| 5,490,982 | 2/1996 | Siciliano . |
| 5,540,853 | 7/1996 | Trinh et al. . |
| 5,587,152 | 12/1996 | Mackles et al. . |
| 5,614,179 | 3/1997 | Murphy et al. . |
| 5,635,166 | 6/1997 | Galleguillos et al. . |
| 5,643,558 | 7/1997 | Provancal et al. . |
| 5,650,143 | 7/1997 | Bergmann et al. . |
| 5,716,604 | 2/1998 | Coe et al. ................................. 424/65 |
| 5,728,762 | 3/1998 | Reich et al. ............................ 524/379 |
| 5,730,963 | 3/1998 | Hilliard, Jr. et al. ..................... 424/65 |

FOREIGN PATENT DOCUMENTS

| | | |
|---|---|---|
| 0 318 206 A1 | 5/1989 | European Pat. Off. . |
| 404 532 A1 | 12/1990 | European Pat. Off. . |
| 0 512 770 A1 | 11/1992 | European Pat. Off. . |
| 0 521 579 A2 | 1/1993 | European Pat. Off. . |
| 0 284 765 B1 | 5/1994 | European Pat. Off. . |
| 96/12468 | 9/1995 | European Pat. Off. . |
| 0714 655 A1 | 11/1995 | European Pat. Off. . |
| 0 714 655 A1 | 6/1996 | European Pat. Off. . |
| 0 512 770 B1 | 10/1996 | European Pat. Off. . |
| 0 770 671 A2 | 5/1997 | European Pat. Off. . |
| 2 062 466 | 5/1981 | United Kingdom . |
| 2 280 111 | 7/1994 | United Kingdom . |
| 91/15191 | 3/1991 | WIPO . |
| 92/19221 | 11/1992 | WIPO . |
| 94/06441 | 9/1993 | WIPO . |
| 95/18599 | 1/1994 | WIPO . |
| 96/32925 | 4/1995 | WIPO . |
| 96/12467-A1 | 9/1995 | WIPO . |
| 97/30689 | 2/1996 | WIPO . |
| 97/30687 | 2/1997 | WIPO . |
| 97/30688 | 2/1997 | WIPO . |
| 97/11671 | 4/1997 | WIPO . |

OTHER PUBLICATIONS

Ralph G. Harry, *Cosmetic Materials—Their Orgin, Characteristics, Uses and Dermatological Action*, by Chemical Publishing Co., Inc., 1963, pp. 354–356.

*Primary Examiner*—Thurman K. Page
*Assistant Examiner*—Susan Tran
*Attorney, Agent, or Firm*—Rosemary M. Miano

[57] ABSTRACT

Cosmetic compositions are disclosed which are made from a multi-component base made from at least three different components, which base exhibits a weight loss not exceeding 46% in a 24 hour period in a controlled environment with minimum air flow in a humidity chamber with a temperature of 35–40 degrees C. and 80% humidity; and a medium volatility fragrance, wherein a solubility parameter is calculated for each of the base and fragrance components are matched so that the difference between them is less than 38%.

12 Claims, No Drawings

PERSONAL HYGIENE PRODUCT WITH ENHANCED FRAGRANCE DELIVERY

FIELD OF THE INVENTION

This invention relates to personal hygiene product compositions which have improved fragrance, especially when formulated into underarm products such as antiperspirants and deodorants.

BACKGROUND OF THE INVENTION

Personal care products such as antiperspirants and/or deodorants have been and continue to be the subject of further refinement and improvement. One of the areas of interest is the incorporation of fragrance into underarm products such as deodorants and antiperspirants to achieve different effects and properties.

Fragrances have been used in a variety of ways in cosmetic products; however, the formulation of cosmetic products with fragrances to achieve good quality products is not always straightforward and reflects a coordination of fragrance (taking into account the compatibility of fragrance with the entire composition), the aesthetics of low skin irritation and good skin feel, and compatibility of various ingredients used in such formulations. The ability to achieve compatibility between all the ingredients, good aesthetics and superior performance in a stable product is further complicated by the form the final product will have (stick, cream, aerosol, etc.).

PCT case WO 97/30689 to The Procter & Gamble Company describes leave-on hair care compositions and leave-on skin care compositions comprising from 0.001–50% of enduring perfume itself comprising at least about 70% of perfume ingredients selected from the group consisting of ingredients having a boiling point of at least about 250 degrees C. and a ClogP of at least 3.

U.S. Pat. No. 5,540,853 to Trinh et al discloses wash off personal treatment compositions and/or cosmetic compositions containing an enduring perfume component meeting a similar description to that described in WO 97/30689.

U.S. Pat. No. 5,409,694 to Meyer et al describes liquid deodorant compositions characterized by the presence of water and zinc phenolsulfonate in selected ratios. These formulations use nonionic emulsifiers, low levels of irritating polyhydric alcohols and relatively low levels of monohydric alcohols.

U.S. Pat. No. 5,587,152 to Mackles et al teach clear, solid, topical deodorant compositions comprising a water-insoluble ester of a water-soluble acid having solubility in water of greater than 50% weight/weight at 20 degrees C., 2–6% by weight of dibenzylidene sorbitol, wherein the compositions are substantially free of water and of water-miscible solvents which are liquid at ambient temperature.

U.S. Pat. No. 5,490,982 to Siciliano discloses cosmetic microemulsion compositions comprising a fragrance and a vehicle system which itself comprises water, isoeicosane and a C8–C40 fatty glyceride alkoxylated with 1–100 moles of C2–C3 alkylene oxide per mole of glycerides.

U.S. Pat. No. 5,614,179 to Murphy et al describes deodorant and antiperspirant/deodorant cosmetic stick and roll-on products with an organic matrix having a dispersed particle phase of an encapsulated bicarbonate salt coated with a film-forming medium itself comprising a blend of a polymer and a fragrance. After application to the underarm surfaces, the fragrance is released. Polyethylene glycol is noted as releasing the fragrance at a relatively fast rate.

U.S. Pat. No. 5,200,174 to describes gel stick antiperspirant compositions comprising a dibenzylidene alditol gelling agent, a 2-oxazolidinone derivative having a C1–C4 alkyl radical substituted at the 3 position of the heterocyclic ring and a hydroxy solvent which itself may be selected from the group consisting of liquid polyethylene glycols, liquid polyethylene glycols, liquid polypropylene polyethylene glycol copolymers, water, C2–C4 alcohols, 2-methoxyethanol, 2-ethoxyethanol, ethylene glycol, 1,2-propylene glycol, 1,3-propylene glycol, 1,4butylene glycol, 1,2-butylene glycol, diethylene glycol monomethylether, diethylene glycol monoethylether, 1,3-butylene glycol, 2,3-butylene glycol, 2,4dihydroxy-2-methylpentane, trimethylene glycol, glycerine, 1,3-butane diol, 1,4butane diol, and mixtures thereof.

U.S. Pat. No. 5,635,188 to Gallefuillos teaches a roll-on or gel antiperspirant comprising an antiperspirant active a carrier and a water soluble or water dispersible hydrophilic polymer having a weight from 5,000–5,000,000 and selected from the group consisting of, for example, polyethylene glycols, polypropylene glycols, polyacrylamides, polymethylacrylamides, polyvinyl alcohols, polyvinyl pyrrolidones, dimethicone copolyols, alkyl dimethicone copolyols, water-soluble cellulosic polymers, hydroxpropylmethylcellulose, carboxymethylcellulose, polyoxyethylene-polyoxypropylene copolymers, polyurethanes, and mixtures thereof.

U.S. Pat. No. 5,417,964 describes a process for manufacturing an antiperspirant stick under selected processing conditions. The carriers incorporated in these compositions may be selected from, for example, non-volatile paraffinic hydrocarbons including polyethylene glycols and polypropylene glycols which have molecular weights in the range of 500–6000.

Commercial products which emphasize the enhancement of fragrance include Old Spice® High Endurance with a dipropylene glycol/propylene glycol system; and Gillette Series Clear Stick Deodorant and Right Guard Clear Stick Deodorant each with a 2-methyl-1,3-propanediol, propylene glycol, dipropylene glycol system. Solid perfume products for application of perfume to areas other than underarms have also been marketed by high-end cosmetic companies over the years, for example, with signature fragrances.

From time to time irritancy problems occur in underarm products, especially deodorants. Selected glycol systems, especially those with higher molecular weight glycols have been suggested to reduce irritation. This may be seen in a copending U.S. patent application Ser. No. 8/689,782, filed on Aug. 18, 1995 assigned to the same owner of this application. Other U.S. patent applications owned by the same owner as this application which are being filed on the even date herewith include U.S. application Ser. No. 09/035, 483, on Mar. 5, 1998, and U.S. application Ser. No. 09/213, 625, filed on Dec. 18, 1998.

There still remains a need, however, for improved cosmetic formulations which exhibit improved durability in fragrance in underarm products and it is an object of the present invention to provide such formulations.

It is also an object of the present invention to provide stick compositions which have acceptable aesthetics while providing enhanced fragrance substantivity in underarm products. These and other objects of the invention will be apparent from the following description.

SUMMARY OF THE INVENTION

The cosmetic compositions of this invention comprise
(a) 40–98%, particularly 60–90%, and more particularly 65–75%, of a multi-component base made from at least three different components, which base exhibits a weight loss not exceeding 46% in a 24 hour period in a controlled environment with minimum air flow in a humidity chamber with a temperature of 35–40 degrees C. and 80% humidity; and
(b) 0.5% to 10%, more particularly 1–3% of a medium volatility fragrance, wherein a solubility parameter is calculated for each of (a) and (b) and are matched so that the difference between (a) and (b) is less than 38%.

DETAILED DESCRIPTION OF THE INVENTION

The base of the present invention comprises a multi-component system made with at least three members of the group consisting of propylene glycol, dipropylene glycol, 2-methyl 1,3 propanediol (also called MPDiol), tripropylene glycol, tetrapropylene glycol, and other polypropylene glycols (also called PPG's) as described below, diethylphthalate, isopropylmyristate, cetyl alcohol, isocetyl alcohol and isostearyl alcohol, wherein the base exhibits a weight loss of less than or equal to 46% in a 24 hour period at a temperature of 32–40 degrees C. and 80% humidity, wherein the multi-component system comprises from 40–98% by weight of the total weight of the composition.

Bases made with more than three components are also included in this invention, for example, those made with four or five components. By way of example, various amounts of each of the components when they are used (based on the total weight of the final cosmetic composition) include:
propylene glycol—1–25%, particularly 10–21%, and more particularly 11–16%;
dipropylene glycol—1–40%, particularly at least 20%;
MPDiol—1–20%, particularly at least 10%;
tripropylene glycol—1–50%, particularly 15–30%;
tetrapropylene glycol—1–50%, particularly 5–15% and more particularly at least 10%;
polypropylene glycol—1–15%, particularly at least 10% of one or more polypropylene glycols having Formula I:

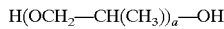

$$H(OCH_2-CH(CH_3))_n-OH \quad \text{Formula I}$$

where n is a number from 5–50, for example, n may be selected from the group consisting of 9, 15, 17, 20, 26, 32, and 35;
isopropylmyristate—1–50%, particularly 5–20% and preferably at least 5%;
diethylphthalate—1–50%, particularly 5–20% and preferably at least 5%;
cetyl alcohol—1–30%, preferably at least 5%;
isocetyl alcohol—1–30%, preferably at least 5%; and
isostearyl alcohol—1–30%, preferably at least 5%;
wherein the multi-component base comprises from 40–98% by weight of the total weight of the cosmetic composition and the amounts are in percent by weight based on the total weight of the composition.

Particular examples of three-component bases include but are not limited to:
(a) dipropylene glycol/tripropylene glycoylpolypropylene glycol, especially where the amount of each component is:

| Deodorant Raw Material | Total Quantity in % (based on the total weight of the final composition) |
|---|---|
| Dipropylene Glycol | 35 |
| Tripropylene Glycol | 21 |
| Polypropylene Glycol - PPG-9 | 14 |

(b) dipropylene glycol/propylene glycoyltripropylene glycol, especially where the amount of each component is:

| Deodorant Raw Material | Total Quantity in % (based on the total weight of the final composition) |
|---|---|
| Propylene Glycol | 14 |
| Dipropylene Glycol | 35 |
| Tripropylene Glycol | 21 | and
(c) dipropylene glycol/propylene glycol/tripropylene glycol, especially where the amount of each component is:

| Deodorant Raw Material | Total Quantity in % (based on the total weight of the final composition) |
|---|---|
| Propylene Glycol | 21 |
| Dipropylene Glycol | 35 |
| Tripropylene Glycol | 14 | wherein the three component base comprises from 60–80%, and preferably 70% by weight of the total cosmetic composition.

Particular examples of a four-component systems include:

| Deodorant Raw Material | Total Quantity in % (based on the total weight of the final composition) |
|---|---|
| Propylene Glycol | 14 |
| Dipropylene Glycol | 21 |
| Tripropylene Glycol | 21 |
| Polypropylene Glycol - PPG-9 | 14 |

Particular examples of a five-component systems include:

| Deodorant Raw Material | Total Quantity in % (based on the total weight of the final composition) |
|---|---|
| Propylene Glycol | 14 |
| Dipropylene Glycol | 14 |
| Tripropylene Glycol | 14 |
| Tetrapropylene Glycol | 14 |
| Polypropylene Glycol - PPG-9 | 14 |

The medium volatility fragrance used in the compositions of this invention is made by combining fragrance components which each have a volatility of 0.0001–0.001 millimeters of mercury (mm Hg) when measured at 25 degrees Celsius and under 760 mm Hg atmospheric. The fragrance components are combined to form a medium volatility fragrance which has a solubility parameter which is within plus or minus 38% of the solubility parameter value of the glycol system used. The medium volatility fragrance may be used as 100% of the overall fragrance in the cosmetic composition, but it must be included in a range of at least 10–40% of the overall fragrance in the cosmetic composition. The levels of fragrance used as a part of the total cosmetic composition will depend on the components used to form the base, but are generally in the range of 0.5 to 10% by weight of the total cosmetic composition, particularly in the range of 1.0–3.0%, or more particularly in the range of 1.5 to 2.5% wherein no more than 50% of the fragrance is a solvent or carrier.

The solubility parameter of the fragrance should also be matched as closely as possible to the solubility parameter of the multi-component mixture. The basic concept of measuring solubility parameters is known from the packaging art and is an expression of the sum of all intermolecular attractive forces empirically related to the mutual solubility of many chemical species. Solubility parameters may be calculated using methods found in the literature, for example, in the *CRC Handbook of Solubility Parameters and Other Cohesion Parameters*, by A. F. Barton (second edition, 1991). Also, software is now available to make such calculations easier, for example, using the Sybyl Molecular Modeling Program 6.03 (available from Tripos Associates, St. Louis, Mo.) to calculate Hildebrand solubility parameters using a structure-property based model. The unit of a solubility parameter measurement is the square root of mole-Pascal.

Sample values for selected solubility parameters include the following:

Solubility parameters for isocetyl alcohol: Solvent molecular weight=242.45 g/mole;
Hildebrand Parameter=17.3 MPa$^{(1/2)}$
Solubility parameters for isostearyl alcohol: Solvent molecular weight=270.50 g/mole;
Hildebrand Parameter=17.1 MPa$^{(1/2)}$
Other examples of values for solubility parameters include:

| Alcohol or Glycol | Solubility Parameter (MPa$^{1/2}$) |
| --- | --- |
| propylene glycol | 26.5 |
| MP-Diol | 24.7 |
| dipropylene glycol | 21.9 |
| tripropylene glycol | 20.0 |
| polypropylene glycol - PPG-9 | 18.2 |
| isocetyl alcohol | 17.3 |
| isostearyl alcohol | 17.1 |

| Fragrance | Solubility Parameter (MPa$^{1/2}$) |
| --- | --- |
| Patchouli alcohol (major component of Patchouli oil) | 13.9 |
| Linalyl acetate (3,7-dimethyl-1,6-octadien-3-yl-acetate | 16.2 |
| Tonalid (6-acetyl-1,1,2,4,4,7-hexamethyltetraline) | 17.2 |
| Linalool (3,7-dimethyl-1,6-octadien-3-ol) | 18.1 |
| Moskene (1,1,3,3,5-pentamethyl-4,6-dinitroindan) | 20.1 |
| Ethyl vanillin (3-ethoxy-4-hydroxybenzaldehyde) | 20.9 |

Examples of suitable fragrances include, but are not limited to, fragrances composed of the following materials having a vapor pressure in the range of 0.01 and 0.0001 mm Hg.

| Aroma Chemical - (Chemical Name) | Vapor Pressure (mm Hg) |
| --- | --- |
| Amyl Cinnamate (isopentyl-3-phenylpropenoate) | 0.0003 |
| Amyl Salicylate (orthohydroxybenzoate) | 0.003 |
| Cedramber (cedryl methyl ether) | 0.0008 |
| Citronellol (3,7-dimethyl-6-octen-1-ol) | 0.009 |
| Dihydroeugenol (2-methoxy-4-propylphenol) | 0.003 |
| Eugenol (2-methoxy-4-allyl phenol) | 0.009 |
| Heliotropine (3,4-methylene-dioxybenzaldehyde) | 0.003 |
| Hexenyl Cinnamate (beta-gamma-hexenylphenyl acrylate) | 0.0001 |
| Hexyl Salicylate (n-hexyl-ortho-hydroxybenzoate) | 0.0007 |
| Indol (2,3-benzpyrrole) | 0.007 |
| Ionone Beta (4-(2,6,6-trimethyl-1-cyclohexen-1-yl)-3-buten-2-one) | 0.006 |
| Iso E Super (7-acetyl,1,2,3,4,5,6,7,8-octahydro-1,1,6,7-tetramethyl naphthalene) | 0.002 |
| Iso Eugenol (2-methoxy-4-propenylphenol) | 0.003 |
| Lillial (alpha-methyl-para-tertiary-butylhydrocinnamic aldehyde) | 0.003 |
| Patchouli Alcohol | 0.0001 |
| Thymol (1-methyl-3-hydroxy-4-isopropyl benzene) | 0.009 |

The overall solubility parameter for each of (a) the medium volatility fragrance and (b) the base is calculated by using normal mathematical principles which sums the portion of each particular fragrance component used times the proportion of that component to the whole. Thus, $$\sum_{i=0}^{i=n} a_i \delta_i$$

which may also be expressed as $$\sum_{i=0}^{i=n} a_i \delta_i = a_1 \delta_1 + a_2 \delta_2 + a_3 \delta_3 + \ldots a_n \delta_n$$

where $a_1+a_2+a_3+a_n=1$

Note that the actual values for the solubility parameters of glycols are close to their theoretical values.

The following two examples of bases show how a single or mixed glycol system can be calculated and matched to a suitable fragrance component on the basis of solubility parameters. In Base I a single glycol, namely propylene glycol, is used in an amount of 70% by weight based on the total weight of the cosmetic product. This component has a solubility parameter of 26.5. In Base II, 14% of propylene glycol having a solubility parameter of 26.5; 35% of dipropylene glycol having a solubility parameter of 21.9; and 21% of tripropylene glycol having a solubility parameter of 20.0 are combined to give a glycol component of 70% by weight based on the total weight of the composition. This mixed glycol component has an overall solubility parameter of 22.25 (calculated by factoring in the various amounts of each component and their particular solubility parameter). Base II would be easier to match to a fragrance listed above on the basis of solubility parameter because 22.25 is closer to the fragrance having a solubility parameter of 20.9 than Base I which has a solubility parameter of 26.5.

An additional feature of this invention is the ability of the cosmetic compositions to sequester various components of malodor in the base. While it is not known exactly how this is achieved, it has been found that the improved performance of deodorant and antiperspirant/deodorant products made according to this invention not only allow for prolonged release and intensity of fragrance, but such products also allow the absorption of a substantial portion (for example, at least 50%, preferably at least 80% and more preferably from 80–100%) of the malodor components of human perspiration, thereby further reducing odor problems associated with sweating.

Other optional ingredients may be included in the cosmetic formulations. In underarm products, especially in deodorant formulations, it may be desirable to add an antibacterial agent. Known bacteriostats include, but not limited to, bacteriostatic quaternary ammonium compounds (for example, cetyl-trimethylammonium bromide), 2-amino-2-methyl-1-propanol (AMP), cetyl pyridinium chloride, 2, 4, 4'-trichloro-2'-hydroxydiphenylether (Triclosan), N-(4-chlorophenyl)-N'-(3,4-dichlorophenyl) urea Triclocarban) and various zinc salts (for example, zinc ricinoleate). The bacteriostat can, illustratively, be included in the composition in an amount of 0.01–2.0%, particularly 0.1–1.0% by weight, of the total weight of the composition. Triclosan, can illustratively be included in an amount of from 0.01% to about 0.5% by weight, of the total weight of the composition and is preferred.

Gelling agent may also be used, especially if stick forms are desired. Suitable gelling agents include at least one member of the group consisting of metallic soaps sodium stearate (for example, sodium stearate and/or sodium isostearate), dibenzylidene sorbitol, a mixed glycol system in combination with dibenzylidene sorbitol, and mixtures of the foregoing. For example, U.S. Pat. No. 5,635,164 describes the use of stearyl alcohol as a gelling agent with sodium chloride as a clarifying agent.

Anti-irritants can also be included in amounts of up to 2% by weight based on the total weight of the composition such as those selected from the group consisting of PEG-40 through PEG-100 Diisostearates (especially PEG-90 Diiostearate available from Scher Chemicals, Inc., West Clifton, N.J.); esters of polyurethane and hydrogenated castor oil; alpha-bisabolol (also called 1-methyl-4-(1,5-dimethyl-1-hydroxyhex4-enyl)cyclohexene); Polyolprepolymer-15 (having a CTFA name of P-8/SMDI Copolymer and a CAS name of poly(oxy- 1 ,2-ethandiyl)-alpha-hydro-omega-hydroxy polymer with 1,1'methylene-bis-(4-isocyanatocyclohexxane)) and available from Penederm Inc., Foster City, Calif.; QuenchT (extracts of mate, kola, and guarana) available from Centerchem, Inc., Stamford, Conn.; solid water soluble polymers containing ethoxylated hydrogenated castor oil (for example, PEG-200 hydrogenated castor oil polymer with IPDI available from Alzo Inc., Matawan, N.J.); PEG-60 almond glycerides (for example, Crovol A-70 available from Croda, Inc. (New York, N.Y.), PEG-20 almond glycerides (Crovol A-40) and mixtures of the foregoing.

Emollients and surfactants may also be included, especially those selected from the group consisting of:
(a) alkoxylated alcohols with a carbon chain length between 2–20 carbons—For example, alkoxylated alcohols wherein the alcohol portion is selected from aliphatic alcohols having 2–18 and more particularly from 4 to 18 carbons, and the alkylene oxide portion is selected from the group consisting of ethylene oxide, polyoxyethylene, and polyoxypropylene having a number of alkylene units from 2–53 (and more particularly from 2 to 15 units) are especially useful. Particular examples include Laureth-4 and Isosteareth-21.

(b) polymeric ethers—for example, Poloxamer 407.
(c) alkoxylated amines—for example, Poloxamine 1307 and Poloxamine 908.
(d) alkoxylated carboxylic acids with a carbon chain length between 2–20 carbons—for example, PEG-100 stearate, PEG-90 Diisostearate.

Examples of suitable materials include isostearyl isostearate, isostearyl palmitate, benzyl laurate, PEG 12 and especially alkyl benzoates such as C 12–C 15 linear alkyl benzoates. The non-volatile emollients can include mixtures. Examples of such mixtures include isostearyl isostearate and C12–C15 alkylbenzoate; and isostearyl benzoate and benzyl laurate.

The compositions of this invention can range from clear to opaque.

Coloring agents may also be used, for example, in an amount of 0.00001–0.5%.

Additional additives for odor absorption can also be included such as sodium bicarbonate.

In one particular stick product a base can be made by combining 10–21% tripropylene glycol; 25–35% dipropylene glycol; 14–24% propylene glycol, 5–10% of at least one gelling agent, where the amounts are based on the total weight of the final cosmetic composition.

Another particular stick product base can be made by combining 10–21% (especially 21%) tripropylene glycol; 25–35% (especially 35%) dipropylene glycol; 14–24% (especially 14%) propylene glycol, 5–10% of at least one gelling agent such as sodium stearate (for example, 7% sodium stearate), 0.05–0.5% (especially 0.2%) stearyl alcohol, 0.05–1.0% (especially 0.5%) sodium chloride, 1.5–2.5% (especially 2%) fragrance, 0.0001–0.005% (especially 0.0014%) coloring agent and 0.05–0.25 (especially 0.05%) of Triclosan, and the remainder as water, where the amounts are based on the total weight of the final cosmetic composition.

The compositions of the invention can be made using conventional techniques. For example, when glycols are used in the multi-component base to make a stick deodorant the following method may be used:
(a) heat the glycols to a temperature of about 85 degrees C.;
(b) add the gelling agent, such as sodium stearate, until it is solubilized in the glycols (water may be added as needed);
(c) cool the mixture to about 80 degrees C.;
(d) optionally add other processing aids such as stearyl alcohol and sodium chloride;
(e) cool the mixture slightly to about 78 degrees C.;
(f) add the fragrance and Triclosan;
(g) cool the mixture to about 70–75 degrees for pouring into containers to cool to room temperature.

Sample formulations for suitable products useful with this invention include the following wherein the amounts are in percent by weight based on the total weight of the composition and anti-irritancy agent is optional:

| Ingredient | range of ingredients | preferred range |
|---|---|---|
| Solid | | |
| Solid #1 | | |
| Solvent (selected from a range of glycols) | 5–88% | 60–75% |
| water | 1–50% | 10–20% |
| compatible gelling agent | 1–10% | 4–8% |
| emollient | 0–5% | 1–2% |

-continued

| Ingredient | range of ingredients | preferred range |
|---|---|---|
| antibacterial agent | 0.01–2.0% | 0.05–0.5% |
| anti–irritancy agent | 0.1–10% | 1–3% |
| fragrance | 0.1–10% | 1–3% |
| Solid #2 (deodorant) | | |
| glycol component (as described above) | 60–98% | 65–75% |
| sodium stearate | 0–10% | 6–8% |
| water | 0–40% | 10–25% |
| fragrance | 0.1–10% | 0.5–3% |
| Solid #3 (antiperspirant/deodorant) | | |
| glycol component (as described above) | 60–98% | 80–95% |
| dibenzylidene sorbitol | 0–5% | 1–3% |
| aluminum zirconium glycine complex | 0–20% | 5–15% |
| fragrance | 0–10% | 0.5–3 |
| Soft solid | | |
| Soft Solid #1 | | |
| solvent (selected from a range of glycols) | 5–88% | 60–75% |
| water | 1–50% | 10–20% |
| ethanol | 1–10% | 2–5% |
| compatible gelling agent | 1–10% | 4–8% |
| emollient | 0–10% | 3–5% |
| antibacterial agent | 0.01–2.0 | 0.05–0.5% |
| anti-irritancy agent | 0.1–10% | 1–3% |
| fragrance | 0.1–10% | 1–3% |
| Soft Solid #2 (antiperspirant/deodorant) | | |
| fatty alcohols | 60–80% | 60–70% |
| volatile silicone | 0–40% | 10–30% |
| aluminum zirconium glycine complex | 10–30% | 15–25% |
| dimethicone copolyol surfactant | 0–3% | 0.3–0.8% |
| clays | 0–5% | 1–3% |
| fragrance | 0.1–10% | 1–3% |
| Flowable gel | | |
| Gel #1 | | |
| solvent (selected from a range of glycols) | 5–88% | 40–50% |
| water | 1–50% | 25–40% |
| ethanol | 1–10% | 2–5% |
| compatible gelling agent | 1–10% | 4–8% |
| emollient | 0–10% | 3–5% |
| antibacterial agent | 0.01–2.0% | 0.05–0.5% |
| anti-irritancy agent | 0.1–10% | 1–3% |
| fragrance | 0.1–10% | 1–3% |
| Gel #2 | | |
| glycol component (as described above) | 60–80% | 60–70% |
| volatile silicone | 0–40% | 20–30% |
| water | 0–20% | 0–10% |
| aluminum zirconium glycine complex | 10–30% | 15–25% |
| dimethicone copolyol surfactant | 0–2% | 0.5–1.5% |
| fragrance | 0.1–10% | 1–3% |
| Cream | | |
| Cream #1 | | |
| solvent (selected from a range of glycols) | 5–88% | 10–20% |
| water | 1–50% | 40–60% |
| compatible gelling agent | 1–10% | 4–8% |
| emollient | 0–10% | 6–8%% |
| Surfactant (Emulsulfier) | 1–10% | 3–5% |
| antibacterial agent | 0.01–2.0 | 0.05–0.5% |
| anti-irritancy agent | 0.1–10% | 1–3% |
| fragrance | 0.1–10% | 1–3% |

-continued

| Ingredient | range of ingredients | preferred range |
|---|---|---|
| Cream #2 | | |
| solvent blend (glycol based) | 60–48% | 60–70% |
| stearic acid | 0–5% | 3–5% |
| water | 0–40% | 10–30% |
| ethyl alcohol | 0–5% | 1–3% |
| color (optional) | 0–1% | 0.05–0.07% |
| fragrance | 0.1–10% | 1–3% |
| Cream #3 (beeswax cream) | | |
| isopropyl myristate (or C16–C24 fatty alcohol | 40–50% | 45–49% |
| beeswax | 10–15% | 12–5% |
| sorbitan stearate | 1–3% | 1.5–2% |
| polysorbate-60 | 3–4% | 3.5–3.9% |
| water | 10–25% | 10–15% |
| glycol mixture | 10–25% | 15–25% |
| fragrance | 0.1–10% | 1–3% |
| Roll-on | | |
| Roll-on #1 (antiperspirant deodorant) | | |
| glycol component | 60–80% | 60–70% |
| volatile silicone | 0–40% | 20–30% |
| water | 0–10% | 2–5% |
| aluminum zirconium glycine complex | 10–30% | 15–20% |
| dimethicone copolyol surfactant | 0–3% | 0.3–0.8% |
| fragrance | 0–10% | 1–3% |

EXAMPLES

The following Examples are offered as illustrative of the invention and are not to be construed as limitations thereon. In the Examples and elsewhere in the description of the invention, chemical symbols and terminology have their usual and customary meanings. Temperatures are in degrees C. unless otherwise indicated. The amounts of the components are in weight percents based on the standard described; if no other standard is described then the total weight of the compositions is to be inferred. Various names of chemical components used in this application include those listed in the *CTFA International Cosmetic Ingredient Dictionary* (Cosmetics, Toiletry and Fragrance Association, Inc., 4th ed. 1991).

Example 1

Batch Making Procedures for Quantities of 100 to 1000 Grams

In three separate glass beakers, the solvents (tripropylene glycol (TPG), dipropylene glycol (DPG) and polypropylene glycol-9 (PPG-9)) were weighed out using a two decimal place analytical balance. These ingredients were added to a large beaker in the following order DPG, TPG and PPG-9. The mixture was then heated to 80 degree Celsius with a hot plate with constant stirring. The temperature was monitored using a resistance thermometer. The beaker was covered with aluminum foil to prevent any material and heat loss. Using a four decimal places analytical balance, Triclosan and stearyl alcohol were weighed and added to the preparation. Sodium stearate was weighed and added slowly to the blend under the same heating and stirring conditions. The blend was stirred until a clear solution was obtained. At this stage, the deionized water and sodium chloride were weighed out and mixed at room temperature. The salt solution was added at 80 degree Celsius with stirring and the mixture was stirred until a clear solution was obtained. The temperature was then reduced to 65 degree Celsius. The fragrance was weighed out and slowly added to the solution using a glass pipette. The blend was then mixed thoroughly for 5 minutes and then poured into appropriate containers. It is preferred that the stirring speed be adjusted for an increase of viscosity at lower temperature. The amounts of materials are:35% dipropylene glycol; 21% tripropylene glycol; 14% polypropylene glycol; 0.05% Triclosan; 7% sodium stearate; 0.5% sodium chloride; 0.2% stearyl alcohol; 2% fragrance; and 20.25% deionized water.

Example 2

The procedure described in Example 1 was repeated using 21% propylene glycol; 35% dipropylene glycol; 14% polypropylene glycol; 0.05% Triclosan; 7% sodium stearate; 0.5% sodium chloride; 0.2% stearyl alcohol; 2% fragrance; and 20.25% deionized water.

Example 3

The procedure described in Example 1 was repeated using 21% MPDiol; 35% dipropylene glycol; 14% polypropylene glycol; 0.05% Triclosan; 7% sodium stearate; 0.5% sodium chloride; 0.2% stearyl alcohol; 2% fragrance; and 20.25% deionized water.

Example 4

The procedure described in Example 1 was repeated using 14% propylene glycol; 35% dipropylene glycol; 21% tripropylene glycol; 0.05% Triclosan; 7% sodium stearate; 0.5% sodium chloride;0.2% stearyl alcohol; 2% fragrance; and 20.25% deionized water.

Example 5

The procedure described in Example 1 was repeated using 21% propylene glycol; 35% dipropylene glycol; 14% tripropylene glycol; 0.05% Triclosan; 7% sodium stearate; 0.5% sodium chloride; 0.2% stearyl alcohol; 2% fragrance; and 20.25% deionized water.

Examples 6–11

For Examples 6–11 the same manufacturing procedure was used as described in Example 1 with the following percent components: 35.00% dipropylene glycol; 21.00% tripropylene glycol; 14% PPG-9; 0.05% Triclosan; 7.00% sodium stearate; 0.50% sodium chloride 0.20% stearyl alcohol and sufficient water to make 99.00% of the composition. The remaining 1.00% was a fragrance listed in Table 6. Note that IBQ is 6-isobutyl quinoline; Iso E is the same as Iso E Super (defined above); Cetalox is a specialty chemical from Firmenich (Princeton, N.J.); Polysantol is 4-penten-2-ol,3,3-dimethyl-5(2,2,3-trimethyl-3-cyclopentenyl-1-yl); ethylene brassylate is 1,13-tridecanedioic acid ethylene ester; Galaxolide is 1,3,4,6,7,8-hexahydro-4,6,6,7,8,8-hexamethylcyclopenta-gamma-2-benzopyran.

TABLE 6

| Fragrance Ingredient | Ex. 6 | Ex. 7 | Ex. 8 | Ex. 9 | Ex. 10 | Ex. 11 |
|---|---|---|---|---|---|---|
| Eugenol | 1.00 | | | | | |
| Amyl salicylate | | 1.00 | | | | |
| Isobutyl quinilone | | | 1.00 | | | |
| Iso E | | | | 1.00 | | |
| Galaxolide | | | | | 1.00 | |
| Ethylene brassylate | | | | | | 1.00 |

Examples 12–17

For Examples 12–17 the same manufacturing procedure was used as described in Example 1 with the following percent components: 21.00% propylene glycol; 35.00% dipropylene glycol; 14.00% tripropylene glycol in Examples 12–15 or 14.00% PPG-9 in Examples 16–17: 0.05% Triclosan; 7.00% sodium stearate; 0.50% sodium chloride 0.20% stearyl alcohol and sufficient water to make 99.00% of the composition. The remaining 1.00% was a fragrance listed in Table 7.

TABLE 7

| Fragrance Ingredient | Ex. 12 | Ex. 13 | Ex. 14 | Ex. 15 | Ex. 16 | Ex. 17 |
|---|---|---|---|---|---|---|
| Amyl salicylate | 1.00 | | | | 1.00 | |
| Iso E | | 1.00 | | | | 1.00 |
| Galaxolide | | | 1.00 | | | |
| Tonalid | | | | 1.00 | | |

Examples 18–22

For Examples 18–22 the same manufacturing procedure as described in Example 1 was used with 7.00% sodium stearate; 0.05% Triclosan; 0.50% sodium chloride; 0.20% stearyl alcohol; 1.70% fragrance; and remaining components listed Table 8 to make 100%.

TABLE 8

| Ingredient | Ex. 18 | Ex. 19 | Ex. 20 | Ex. 21 | Ex. 22 |
|---|---|---|---|---|---|
| MPDiol | | | 10.50 | 7.50 | |
| dipropylene glycol | 35.00 | 42.00 | 45.50 | 38.50 | 35.00 |
| tripropylene glycol | 21.00 | 21.00 | | | 15.00 |
| PPG-9 | 14.00 | 7.00 | 14.00 | 14.00 | 14.00 |
| deionized water | 20.55 | 20.55 | 20.55 | 20.55 | 26.55 |

Examples 23–26

For Examples 23–26 the same manufacturing procedure as described in Example 1 was used with the 35% dipropylene glycol; 14% PPG-9; 0.05% Triclosan; 7% sodium stearate; 0.50% sodium chloride; 0.20% stearyl alcohol; and the remainder as the following percent components listed in Table 9:

TABLE 9

| Ingredient | Example 23 | Example 24 | Example 25 | Example 26 |
|---|---|---|---|---|
| propylene glycol | | | | 21.00 |
| tripropylene glycol | 21.00 | 21.00 | 21.00 | |
| fragrance | 1.70 | 2.00 | 2.30 | 2.00 |
| deionized water | 20.55 | 20.25 | 19.95 | 20.25 |
| Total | 100.00 | 100.00 | 100.00 | 100.00 |

Example A—Preparation of Samples for Malodor Reduction Evaluation by Static Headspace Gas Chromatoraphic Technique A weighed amount of a mixture of C7 acids containing the isomers 3-methyl hexanoic acid, cis-3-methyl-2-hexanoic acid and trans-3-methyl-2-hexanoic acid ("TMHA") the main component of underarm malodor) is diluted with ethanol to give a concentration of 10 mg/ml of acid in alcohol (malodor solution). For each test two non-woven cotton pads (Webril® pads from Kleen Test, West Parkland Court, Milwaukee, Wis.) are cut to be about 12 cm² (3 cm×4 cm) in area. A 200 mg sample of the product to be tested is applied to one pad. The cotton pad is placed in an open Petri dish and placed in a fume hood for 30 minutes to allow the fragrance level to diminish. The second pad is also placed in a Petri dish but is not treated with product and serves as a blank. A 0.2 ml aliquot ( 2 mg of acids) of the malodor solution described above is applied to each of the pads and the pads are placed in the fume hood for an additional 1 hour to allow the ethanol to evaporate. Each pad is then crimp sealed in a separate 22 ml automatic headspace sample vial with an aluminum-backed septum cap. In the case where the effects of aging upon odor absorption are evaluated, both the product-treated and untreated Webril® pads are placed in a humidity chamber at 40 degrees C. and 80% humidity for a designated period of time (for example, 12 hours or 24 hours). At the end of the period the pads are removed from the chamber and allowed to cool to room temperature prior to the addition of the malodor solution. Following this step, the pads are placed in a fume hood for one hour then sealed in a headspace vial as described above. Analysis may then be performed on a Perkin-Elmer HS-40 (or equivalent) autosampling and equilibration unit interfaced to a Hewlett Packard 5890 gas chromatograph fitted with a fused silica capillary column and flame ionization detector ("FID"). Typical conditions for the headspace GC analysis are: sample equilibration temperature—75 degrees C.; equilibration time—60 minutes; needle temperature—78 degrees; transfer line temperature—140 degrees C.; pressurization time—2 minutes; injection time—0.25 min.; withdraw time—0.5 minutes; GC cycle time—35 minutes. Typical GC conditions are: Column—Stabilwax 30 m×0.32 mm (0.25 micron coating); carrier gas—helium; electronic pressure program—21 pounds per square inch at 50 degrees C.; flow rate—2.1 ml/min; detector temperature—240 degrees C.; injector temperature—225 degrees C.; initial oven temperature—50 degrees C.; initial time—0.5 min; temperature ramp—6 degrees/min; final oven temperature—175 degrees C.; final time—1.0 min; injection mode—splitless.

After the analysis by headspace GC is completed, the effectiveness of the product in eliminating malodor, expressed as a percentage reduction in the malodor headspace vapor pressure, is determined. This is done by comparing the level of malodor in the vial containing the treated pad versus the untreated pad and is illustrated by the following calculation:

% reduction in the level or malodor =

$$\frac{(D2 \text{ total peak area} - D1 \text{ total peak area})}{D2 \text{ total peak area}} \times 100$$

D2 total peak area where D2 is equal to the sum of the GC peak areas of 3-methyl hexanoic acid, cis-3-methyl-2-hexanoic acid and trans-3-methyl-2-hexanoic acid present on the untreated (blank) pad, and D1 represents the total GC peak area of the same three acids present on the pad treated with 200 mg of the gel or product. In the above equation the total peak area of the cis- and trans-3-methyl-2-hexanoic acids may be used without significantly affecting the result.

Examples A1–A6

To perform this evaluation samples were made using the method described in Example 1 with the percent of ingredients shown in Table II or obtained as being commercial products. Percent malodor reduction was evaluated using the method described in Example A and the resulting data is shown in Table 12.

TABLE 11

| Ingredient | Ex. A1 | Ex. A2 Commercial Product A[1] | Ex. A3 | Ex. A4 | Ex. A5 | Ex. A6 Commercial Product B[1] |
|---|---|---|---|---|---|---|
| propylene glycol | | | 21 | 21 | | |
| dipropylene glycol | 35 | | 35 | 35 | 35 | |
| tripropylene glycol | 21 | | 14 | | 21 | |
| PPG-9 | 14 | | | 14 | 14 | |
| Triclosan | 0.05 | | 0.05 | 0.05 | 0.05 | |
| sodium stearate | 7 | | 7 | 7 | 7 | |
| sodium chloride | 0.5 | | 0.5 | 0.5 | 0.5 | |
| stearyl alcohol | 0.2 | | 0.2 | 0.2 | 0.2 | |
| fragrance | 1.7 | | | | | |
| deionized water | 20.55 | | 22.5 | 22.5 | 22.5 | |
| Total | 100.00 | 100.00 | 100.00 | 100.00 | 100.00 | 100.00 |

(1)Commercial products.

TABLE 12

Percent Malodor Reduction

| Aging Time | Ex. A1 | Ex. A2 | Ex. A3 | Ex. A4 | Ex. A5 | Ex. A6 |
|---|---|---|---|---|---|---|
| 0 hours | 96.5 (1.9) | 92.4 (2.9) | 92.4 (3.2) | 90.6 (06) | 89 (1.6) | 92.7 (2.6) |
| 12 hours | 95.5 (2) | 74.3 (6.2) | — | — | — | 86 (2.7) |
| 24 hours | 92.3 (1.5) | 72.1 (6.7) | 91.2 (0.9) | 86.2 (7.7) | 91.9 (1) | 86.2 (5) |

Numbers in parentheses indicate percent relative standard deviation. Some contribution from fragrance to the absorption of malodor may be taking place in samples A1 and A5. Data shows that formulations of the invention are better than or equal to the commercial products tested.

Examples A7–A 13

A set of samples were made using the method as described in Example 1 with the following percentages of ingredients: 14.00% propylene glycol; 35% dipropylene glycol; 21% tripropylene glycol; 0.05% Triclosan; 7% sodium stearate; 0.5% sodium chloride; 0.20% stearyl alcohol; 0.4% coloring agent with various amounts of fragrance and sufficient deionized water to make 100%. The fragrance amounts were 2% for Examples A7 and A8; 2.25% for Example A11; 2.5% for Examples A10 and A12; and 1.8% for Example A9. Example A 13 did not have added fragrance. The percent malodor reduction was evaluated as described above and the data is shown in Table 13. Notes from Table 12 apply here also.

TABLE 13

Percent Malodor Reduction

| Aging Time | Ex. A6 Commercial Product | Ex. A7 | Ex. A8 | Ex. A9 | Ex. A10 | Ex. A11 | Ex. A12 | Ex. A13 |
|---|---|---|---|---|---|---|---|---|
| 0 hours | 93.5 (1.8) | 91.4 (4.2) | 93.6 (2.2) | 99.4 (.05) | 91.5 (4.7) | 93.2 (2.4) | 92.2 (1.5) | 95 (2) |
| 12 hours | 89.7 (3) | 94.6 (1.4) | 90.7 (2.1) | 91.9 (0.3) | 91.2 (4.2) | 93.2 (0.5) | 93.2 (2.6) | 91.9 (4.2) |
| 24 hours | 88.9 (0.6) | 90.5 (1.7) | 92.8 (1.8) | 89 (1.6) | 88.9 (3.5) | 92.8 (2.3) | 92.8 (2) | 89.2 (2.1) |

EXAMPLE B
Procedure for Evaluating Weight Loss

Samples were made using the method described in Example 1. For evaluating the samples a precisely weighed quantity of deodorant product (0.5 grams) was applied to the surface of a cotton pad. The weight of the sample (product+pad) was recorded using an analytical balance with two decimal places. The sample was placed in a humidity oven at 40 degrees C. and 80% humidity for 12 or 24 hours. The weight of the sample was recorded after aging. Each formulation was tested in triplicate and the average value of the three runs was reported. The equation used to calculate weight loss in percent was:

percent weight loss=100×(Wo−Wt)/Wp where Wo is the initial weight of the sample, Wt is the weight of the same sample after aging for the selected time period (12 or 24 hours) and Wp is the weight of the product applied to the pad. (0.5 grams). The results indicate that all the products using the glycol blend system provide a weight loss less than or equal to 46% (±5%) of the original weight after 24 hours, indicating a longer lasting fragrance capability for such a base.

The procedure described in Example B was used to evaluate the samples described in Examples B1 –B7 and Control sample C1 for the times indicated in Tables 10 and I1. The samples were made in 500 gram batches using the percent components as follows. The common ingredients for all of these examples included 7.00% of sodium stearate (except for Example B7 which used 6.00%); 0.50% sodium chloride; 0.20% stearyl alcohol; 2.00% fragrance; 0.05% Triclosan; 14.00% PPG-9; and sufficient deionized water to make 100.00%. The additional ingredients that were varied and the data for weight loss in percents are shown in Tables 14 and 15. The control sample had a weight loss greater than 46%.

TABLE 14

| Formula Component | Example B1 | Example B2 | Example B3 | Example B4 |
|---|---|---|---|---|
| propylene glycol | | 21.00 | | 1.00 |
| MPDiol | | | 21.00 | 20.00 |
| dipropylene glycol | 35.00 | 35.00 | 35.00 | 35.00 |
| tripropylene glycol | 21.00 | | | |
| weight loss after 12 hours | 8.00 | 28.00 | 12.00 | 8.00 |
| weight loss after 24 hours | 8.00 | 36.00 | 16.00 | 16.00 |

TABLE 15

| Formula Component | Example B5 | Example B6 | Example B7 | Example B8 | Control C1 |
|---|---|---|---|---|---|
| propylene glycol | 13.00 | 13.00 | 11.00 | 15.00 | 56.00 |
| MPDiol | 20.00 | 20.00 | 11.00 | | |
| dipropylene glycol | 23.00 | | 17.00 | 25.00 | |
| tripropylene glycol | | 23.00 | 17.00 | 10.00 | |
| weight loss after 12 hours | 24.00 | 24.00 | 28.00 | 36.00 | 54.00 |
| weight loss after 24 hours | 38.00 | 36.00 | 38.00 | 46.00 | 66.00 |

EXAMPLE C
Evaluation of Samples for Fragrance Endurance (Substantivity)

Samples were prepared using the method described in Example 1 using the amounts of materials listed in Tables 16 and 17. For Examples F1–F7 the common ingredients included 35% dipropylene glycol; 21% tripropylene glycol; 14% PPG-9; 0.05% Triclosan; 7% sodium stearate; 0.05% sodium chloride; 0.2% stearyl alcohol and sufficient deionized water to make 99.0%. The remaining 1% of material to make a composition of 100.0% was selected from the fragrance material listed in Table 16. For Examples CX1–CX7 the common ingredients were 70% propylene glycol; 0.05% Triclosan; 7% sodium stearate; 0.5% sodium chloride; 0.2% stearyl alcohol; and sufficient deionized water to make 99.0%. The remaining 1.0% of material to make a composition of 100.0% was selected from the fragrance material listed in Table 16.

In order to evaluate the fragrance endurance a measured amount of the composition (0.50 grams) was applied as a thin layer at the surface of a 5 cm—5 cm Webril® pad. The pads were then introduced in a humidity oven at 40 degrees C. and 80% humidity for 24 hours. Each of these samples was then placed in headspace vials using a pair of tweezers. The vials were sealed immediately after incorporation of the sample. The samples were analyzed using headspace gas chromatography. The gas chromatograph (Hewlett Packard 5890 II) was equipped with a flame ionization detector.

For stick samples a known quantity (150 mg unless otherwise specified) was applied to the surface of a Webril® pad. The sample (pad+applied formulation) was placed in a humidity oven at 40 degrees C. and 80% humidity for a fixed time, removed and promptly placed in sealed headspace vials for further analytical tests or glass jars for sensory evaluation.

Static headspace analysis was done on selected samples by using a headspace sampler (HS 40 from Perkin-Elmer) operating (unless otherwise specified) with the following conditions: sample temperature 60 degrees C.; injection time 0.1 minute transfer temperature 110 degrees C.; GC cycle time 32 minutes. The headspace samples were analyzed using a gas chromatograph (HP 5890 Series II Hewlett-Packard) with a Stabilwax polar column. Empty vials were placed with several blanks between to prevent contamination. For this GC the oven temperature was 50 degrees C.; initial time was 1 minute; final temperature was 240 degrees C.; hold tie was 5.25 minutes; injections and detector temperatures were both 250 degrees C.; and column length was 30 meters. The results are reported in terms of area under the curve (AUC units). The glycol blend showed superior results as compared to the simple glycol base. The results are listed in Tables 16 and 17. The results obtained with compositions of the invention (Examples F1–F7) may be compared to the control samples (Examples CX1–CX7). The definitions for the fragrances have been previously given.

TABLE 16

| Fragrance | Ex. F1 | Ex. F2 | Ex. F3 | Ex. F4 | Ex. F5 | Ex. F6 | Ex. F7 |
|---|---|---|---|---|---|---|---|
| Eugenol | 1.0 | | | | | | |
| Amyl salicylate | | 1.0 | | | | | |
| Isobutyl quinoline ("IBQ") | | | 1.0 | | | | |
| Iso E | | | | 1.0 | | | |
| Ethylene brassylate | | | | | 1.0 | | |
| Cetalox | | | | | | 1.0 | |
| Polysantol | | | | | | | 1.0 |
| AUC units | 665 | 6677 | 2979 | 4570 | 1301 | 1727 | 12140 |

TABLE 17

| Fragrance | Ex. CX1 | Ex. CX2 | Ex. CX3 | Ex. CX4 | Ex. CX5 | Ex. CX6 | Ex. CX7 |
|---|---|---|---|---|---|---|---|
| Eugenol | 1.0 | | | | | | |
| Amyl salicylate | | 1.0 | | | | | |
| IBQ | | | 1.0 | | | | |
| Iso E | | | | 1.0 | | | |
| Ethylene brassylate | | | | | 1.0 | | |
| Cetalox | | | | | | 1.0 | |
| Polysantol | | | | | | | 1.0 |
| AUC units | not detectable | 1549 | 1156 | 1292 | not detectable | 595 | 1541 |

While the compositions have emphasized deodorants it is to be noted that antiperspirant actives such as those conventionally used may be included for example as suspensions or solutions or added directly during mixing. If it is desired to form cosmetic products with an antiperspirant claim and/or action, an antiperspirant active material should also be included in the composition. Various antiperspirant active materials that can be utilized according to the present invention include conventional aluminum and aluminum/zirconium salts, as well as aluminum/zirconium salts complexed with a neutral amino acid such as glycine, as known in the art See each of EPA No. 512,770A1 and PCT No. WO92/19221, the contents of each of which are incorporated herein by reference in their entirety, for disclosure of antiperspirant active materials. The antiperspirant active materials disclosed therein, including the acidic antiperspirant materials, can be incorporated in the compositions of the present invention. Suitable materials include (but are not limited to) aluminum chlorohydroxide, aluminum chloride, aluminum sesquichlorohydroxide, zirconyl hydroxychloride, and aluminum chlorohydrol-propylene glycol complex. These include, by way of example (and not of a limiting nature), aluminum chlorohydrate, aluminum chloride, aluminum sesquichlorohydrate, zirconyl hydroxychloride, aluminum-zirconium glycine complex (for example, aluminum zirconium trichlorohydrex gly, aluminum zirconium pentachlorohydrex gly, aluminum zirconium tetrachlorohydrex gly and aluminum zirconium octochlorohydrex gly), aluminum chlorohydrex PG, aluminum chlorohydrex PEG, aluminum dichlorohydrex PG, and aluminum dichiorohydrex PEG. The aluminum-contaiing materials can be commonly referred to as antiperspirant active aluminum salts. Generally, the foregoing metal antiperspirant active materials are antiperspirant active metal salts. In the embodiments which are antiperspirant compositions according to the present invention, such compositions need not include aluminum-containing metal salts, and can include other antiperspirant active materials, including other antiperspirant active metal salts. Generally, Category I active antiperspirant ingredients listed in the Food and Drug Administration's Monograph on antiperspirant drugs for over-the-counter human use can be used. In addition, any new drug, not listed in the Monograph, such as aluminum nitratohydrate and its combination with zirconyl hydroxychlorides and nitrates, or aluminum-stannous chlorohydrates, can be incorporated as an antiperspirant active ingredient in antiperspirant compositions according to the present invention. Preferred antiperspirant actives that can be incorporated in the compositions of the present invention include the enhanced efficacy aluminum salts and the enhanced efficacy zirconium/aluminum salt-glycine materials, having enhanced efficacy due to improved molecular distribution, known in the art and discussed, for example, in PCT No. WO92/19221, the contents of which are incorporated by reference in their entirety herein.

The amount of antiperspirant active material incorporated in the stick composition of the present invention is, preferably, an antiperspirant effective amount; that is, an amount to reduce the flow of perspiration from the location (for example, axillary region of a human) to which the antiperspirant is applied. For deodorant products a level of from 0.5–20%, more particularly 0.5–5.0% by weight based on the entire weight of the composition is used. For an antiperspirant product an amount of 5.0–25%, particularly 5–20%, even more particularly 7–15%, and especially 7–12% by weight based on the total weight of this composition may be used. The amount of antiperspirant material utilized is dependent on the efficacy of the specific antiperspirant material, as well as a maximum amount which avoids a reduction in clarity of the final product.

For embodiments of the invention which contain an antiperspirant (either at a level denominated "deodorant" or at a level denominated "antiperspirant") it is preferred that a stabilizing agent also be included Examples of suitable stabilizing agents include cosmetically acceptable alkali metal salts, bases, amines and other nitrogen containing compounds, particularly guanidine carbonate (described in U.S. Pat. No. 5,490,979 and assigned to the same owner as this application).

We claim:

1. A cosmetic composition comprising;
   (a) 40–98% of a multi-component base made from at least three different components, which base exhibits a weight loss not exceeding 46% in a 24 hour period in a controlled environment with minimum air flow in a humidity chamber with a temperature of 35–40 degrees C. and 80% humidity; and
   (b) 0.5% to 10% of a medium volatility fragrance,
   wherein a solubility parameter is calculated for each of (a) and (b) and the solubility parameters are matched so that the difference between (a) and (b) is less than 38% and amounts are in percent by weight based on the total weight of the cosmetic composition, wherein the multi-component base is made with at least three members of the group selected from the group consisting of diethylphthalate; isopropylmyristate; cetyl alcohol; isocetyl alcohol; isostearyl alcohol; propylene glycol; dipropylene glycol; tripropylene glycol- tetrapropylene glycol; and polypropylene glycols selected from glycols of Formula 1:

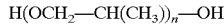

H(OCH$_2$—CH(CH$_3$))$_n$—OH          Formula I where n is a number from 5–50,
   wherein the multi-component base is made with at least three components selected from the group consisting of 1–25% propylene glycol; 1–40% dipropylene glycol; 1–50% tripropylene glycol; 1–50%; 1–15% polypropylene glycol; 1–50% isopropylmyristate; 1–50% diethylphthalate; 1–30% cetyl alcohol; 1–30% isocetyl alcohol; an 1–30% isocetyl alcohol wherein the amounts are in percent by weight based on the total weight of the composition wherein the multi-component base comprises from 40–98% by weight of the total weight of the composition.

2. A cosmetic composition according to claim 1 wherein the composition comprises 60–90% of the multi-component base.

3. A cosmetic composition according to claim 1 wherein the composition comprises 65–75% of the multi-component base.

4. A cosmetic composition according to claim 1 wherein the composition comprises 1–3% of the medium volatility fragrance.

5. A cosmetic composition according to claim 1 wherein the multi-component base is made with at least three components selected from the group consisting of 10–21% propylene glycol; 20–40% dipropylene glycol; 15–30% tripropylene glycol; 15–15%; 10–15% polypropylene glycol; 5–20% isopropylmyristate; 5–20% diethylphthalate; 5–30% cetyl alcohol; 5–30% isocetyl alcohol; and 5–30% isostearyl alcohol.

6. A cosmetic composition according to claim 1 further comprising at least one member from the group consisting of:
   (a) antiperspirant active ingredients;
   (b) fragrances;
   (c) antibacterial agents;
   (d) anti-irritants;
   (e) emollients; and
   (f) surfactants.

7. A cosmetic composition according to claim 1 made by combining 10–21% tripropylene glycol; 25–35% dipropylene glycol; and 14–24% propylene glycol.

8. A cosmetic composition according to claim 1 further comprising 5–10% of at least one gelling agent.

9. A cosmetic composition according to claim 1 made by combining 10–21% tripropylene glycol; 25–35% dipropylene glycol; 14–24% propylene glycol, 5–10% of at least one gelling agent, and 0.05–0.5% antibacterial agents.

10. A cosmetic composition according to any one of claims 1–4 and 5–9 wherein the cosmetic composition is a deodorant.

11. A cosmetic composition according to any one of claims 1–4 and 5–9 wherein the cosmetic composition further comprises a cosmetically active ingredient.

12. A cosmetic composition according to claim 8 wherein the gelling agent is selected from the group consisting of at least one member of the group consisting of
   (a) dibenzylidene sorbitol; (b) a mixed glycol system in combination with dibenzylidene sorbitol; and mixtures of (a) or (b) in combination with one or more members selected from the group consisting of sodium stearate and sodium, isostearate.

* * * * *